US00PP16589P2

(12) United States Plant Patent
Snoeijer

(10) Patent No.: US PP16,589 P2
(45) Date of Patent: May 30, 2006

(54) ***CLEMATIS* PLANT NAMED 'HENDRYETTA'**

(50) Latin Name: ***Clematis*×*hybrida***
Varietal Denomination: Hendryetta

(76) Inventor: Wim Snoeijer, Vest 1b2, Gouda S-H 2801 TX (NL)

( * ) Notice: Subject to any disclaimer, the term of this patent is extended or adjusted under 35 U.S.C. 154(b) by 126 days.

(21) Appl. No.: 10/916,349

(22) Filed: Aug. 10, 2004

(51) Int. Cl.
*A01H 5/00* (2006.01)

(52) U.S. Cl. ..... Plt./228

(58) Field of Classification Search ..... Plt./228
See application file for complete search history.

*Primary Examiner*—Kent Bell

(57) ABSTRACT

A new cultivar of *Clematis* named 'Hendryetta' that is characterized by a low growing, upright, semi-climbing habit, symmetrical light purple flowers which are fragrant, and medium to dark-green foliage. In combination these traits set 'Hendryetta' apart from all other existing varieties of *Clematis* known to the inventor.

2 Drawing Sheets

Genus: *Clematis*.
Species: ×*hybrida*.
Denomination: Hendryetta.

BACKGROUND OF THE INVENTION

The present invention relates to a new and distinct cultivar of *Clematis* that is grown for use as an ornamental in the landscape. The new cultivar is known botanically as *Clematis* and will be referred to hereinafter by the cultivar name 'Hendryetta'.

*Clematis* is an important commercial genus with a large number of cultivar hybrids accumulated over a long period. The Inventor feels that modern gardens are unsuited to the vigorous large-flowered hybrids mostly in commerce. In 1990, the Inventor commenced a formal breeding program in Boskoop, Holland, whose purpose is to produce free-flowering *Clematis* plants that are easy to propagate and which are shorter in eventual height and which flower at a shorter height than many cultivars of *Clematis* in commerce.

In 1992, the Inventor successfully pollinated the female parent plant *Clematis* hybrid 'Purpureostriata' (unpatented) with male parent plant *Clematis* hybrid 'Aljonushka' (unpatented). *Clematis* 'Aljonushka' has been granted an Award of Garden merit by The Royal Horticultural Society of England. Very few seeds resulted and one seedling, later named 'Hendryetta', was selected in 1996 as having distinct and desirable characteristics, namely, a tidy and very upright habit, tendency to bear flowers along the stem rather than predominantly at the terminals, and flowers which are a light purple color and which are fragrant.

When compared with the male parent, *Clematis* 'Aljonushka', whose flowers are of a similar color, 'Hendryetta' is approximately one half to two-thirds shorter in overall height.

When compared with the female parent, *Clematis* 'Purpureostriata', 'Hendryetta' exhibits simple or ternate leaves and is more floriferous. The leaves of *Clematis* 'Purpureostriata' are distinctly pinnate.

Apart from the parental cultivars, the closest comparison variety known to the Inventor is *Clematis* hybrid 'Heather Herschell' whose flowers have tepals which are more recurved and twisting, whereas the flowers of 'Hendryetta' are symmetrical and bell-shaped, with little or no reflexing. In addition, the stated height of *Clematis* 'Heather Herschell' is in the range 2.0 m to 2.6 m whereas the typical height of 'Hendryetta' is 1.0 m to 1.8 m.

The first asexual propagation of 'Hendryetta' was accomplished by the inventor in 1996 in a cultivated area of Boskoop, Holland, using softwood cuttings. After conducting successive cycles of asexual reproduction, the Inventor has determined that new cultivar 'Hendryetta' is stable and reproduces true to type.

An application for a grant of European Community Plant Breeders Rights was filed for 'Hendryetta' on Nov. 8, 2002, Application Number 2002/1772. A grant of European Community Plant Breeders Rights was issued on Jun. 7, 2004, Ser. No. 13548.

'Hendryetta' was first exhibited to the public at the Plantarium Exhibition, Boskoop, The Netherlands, on Aug. 20, 2003 at which it was awarded a prize for "Best Novelty". The first orders for purchase of plants of Hendryetta were taken during the Plantarium show and the first delivery of a plant of 'HENDRYETTA' took place on Sep. 2, 2003.

SUMMARY OF THE INVENTION

The distinguishing characteristics of the new *Clematis* cultivar 'Hendryetta' are as follows. In combination, these traits set 'Hendryetta' apart from all other existing varieties of *Clematis* known to the inventor. *Clematis* 'Hendryetta' exhibits light purple flowers.

1. *Clematis* 'Hendryetta' is floriferous.
2. *Clematis* 'Hendryetta' is readily propagated using softwood cuttings.
3. *Clematis* 'Hendryetta' exhibits an upright to semi-climbing habit.
4. The flowers of *Clematis* 'Hendryetta' are elegant, symmetrical, bell-shaped.
5. The flowers of *Clematis* 'Hendryetta' are fragrant.
6. *Clematis* 'Hendryetta' exhibits medium to dark-green foliage.

'Hendryetta' has not been tested under all possible conditions and phenotypic differences may be observed with variations in environmental, climatic, and cultural conditions, however, without any variance in genotype.

BRIEF DESCRIPTION OF THE DRAWINGS

The accompanying color drawings illustrate the overall appearance of the new *Clematis* variety 'Hendryetta' showing the colors as true as it is reasonably possible to obtain in colored reproductions of this type. Colors in the drawings may differ from the color values cited in the detailed botanical description, which accurately describes the actual colors of the new variety 'Hendryetta'.

The drawing labeled as FIG. 1 illustrates a whole plant which is approximately fifteen months old from a cutting. The cutting was rooted in a frost-protected greenhouse in spring 2003, potted outside in a 1-liter container in summer 2003, cut back to 15 cm above the pot in the fall of 2003, over wintered under frost-protected glass, and allowed to grow and vine and flower outside in the spring and early summer of 2004. The entire growth cycle took place at the Inventor's nursery in Boskoop, The Netherlands.

Figure 1:
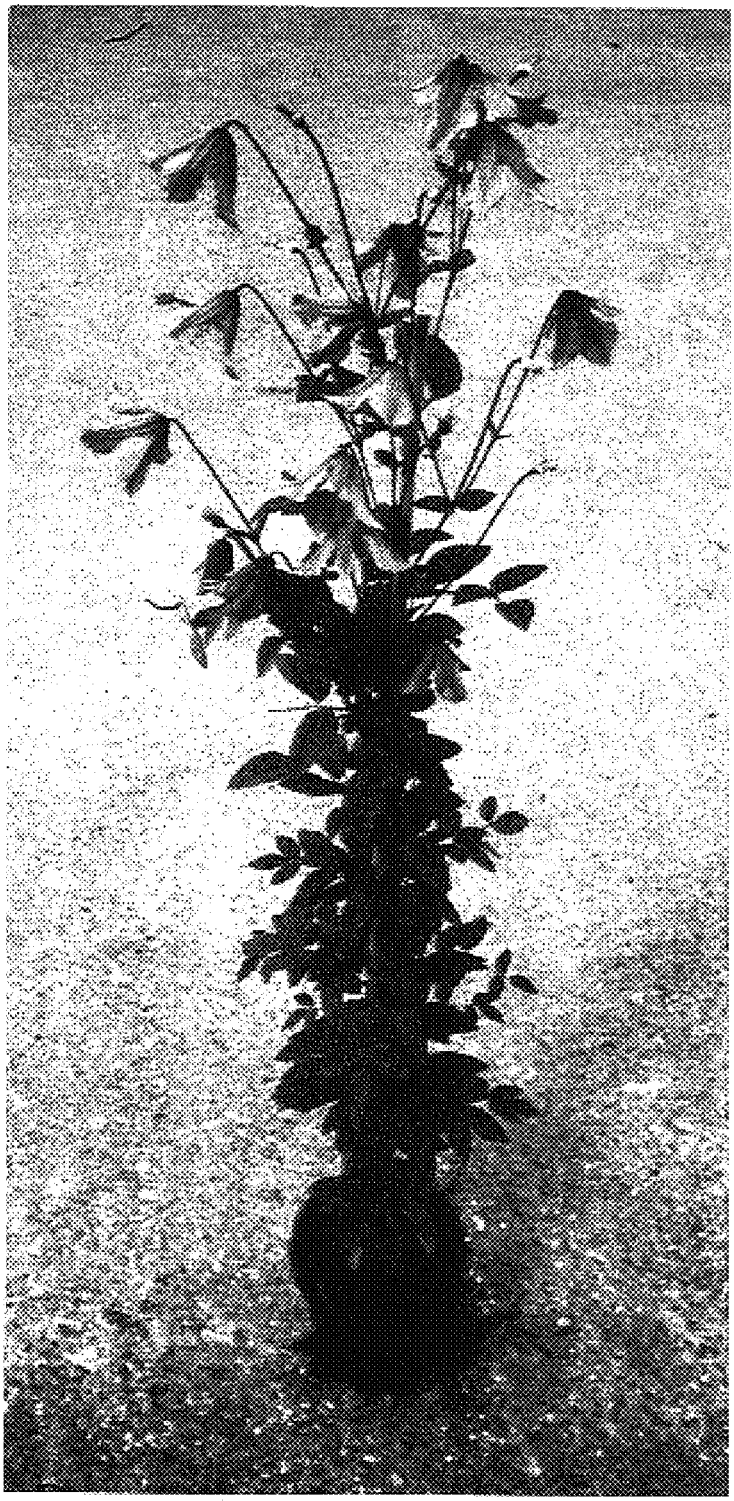
Figure 2:
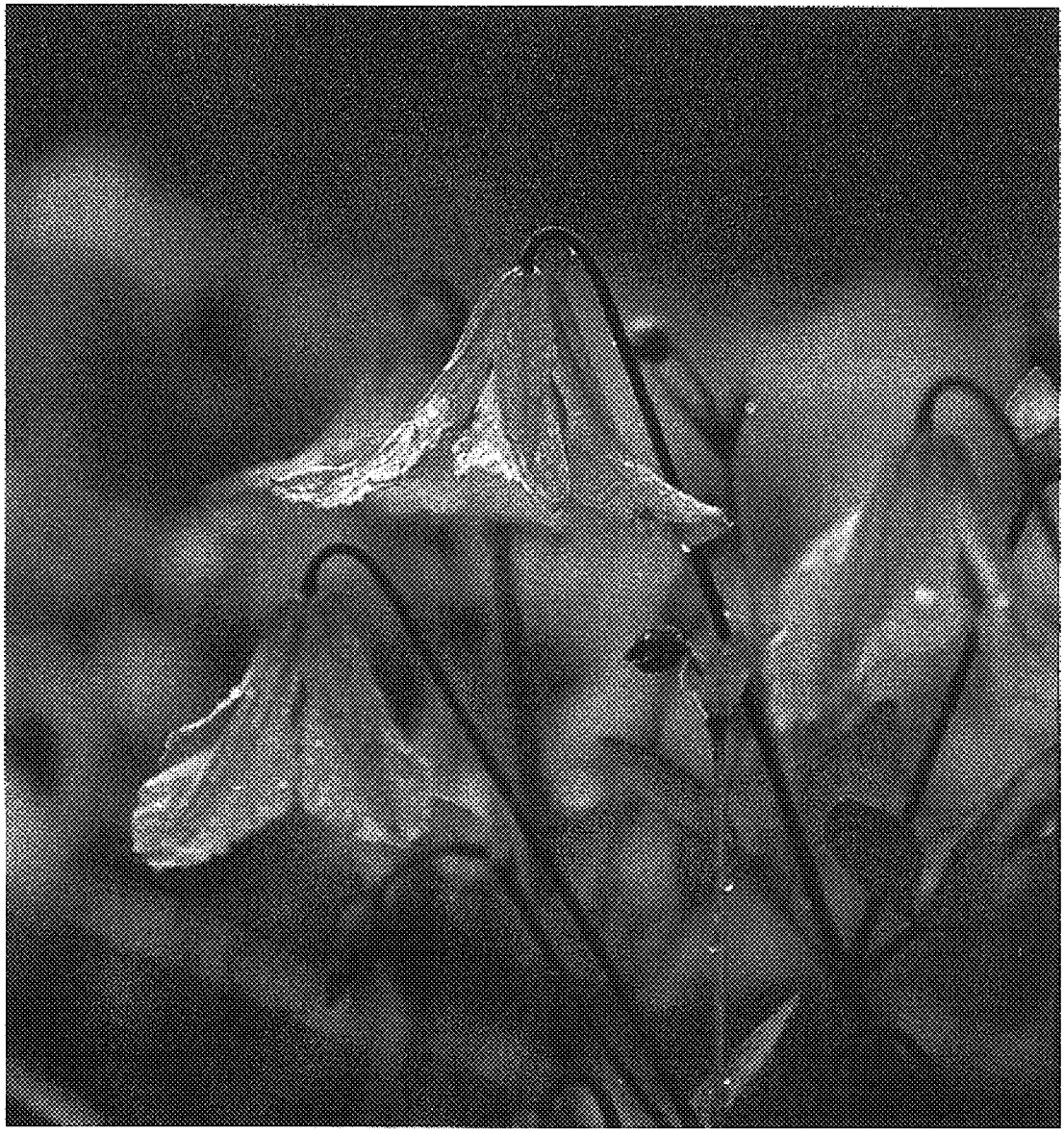

The drawing labeled as FIG. 2 presents a close up view of the flowers and illustrates the two-tone coloration of the upper surface of the tepals and the red-purple coloration of the peduncles.

Both drawings were made using conventional techniques and although foliage and flower colors may appear different from actual colors due to light reflectance, they are as accurate as possible by conventional photography.

BOTANICAL DESCRIPTION OF THE PLANT

The following is a detailed description of the *Clematis* cultivar named 'Hendryetta'.

Data was collected in Boskoop, Holland from a 15 months old plant which had been grown as follows: A cutting of 'Hendryetta' was rooted in a frost-protected greenhouse in spring 2003, potted outside in a 1-liter container in summer 2003, cut back to 15 cm above the pot in the fall of 2003, over wintered under frost-protected glass, and allowed to grow and vine and flower outside in the spring and early summer of 2004. The entire growth cycle took place in Boskoop, The Netherlands.

Color determinations are in accordance with the 2001 Royal Horticultural Society Colour Chart except where general color terms of ordinary dictionary significance are used. The growing requirements are similar to the species.

Botanical classification: *Clematis* 'Hendryetta' (Diversifolia group).
Species: ×*hybrida*.
Common name: Vase vine.
Use: Ornamental.
Parentage: 'Hendryetta' is a hybrid plant that resulted from the hybridization of the following parent plants:
  *Male parent.*—*Clematis* 'Aljonushka'.
  *Female parent.*—*Clematis* 'Purpureostriata'.
Type: Perennial.
Vigor: Low vigor.
Sexuality: Bisexual.
Habit: Upright to semi-climbing.
Height (at maturity): 180 cm. in height.
Width (at maturity): 50 cm. in width.
Hardiness: USDA Zone 5.
Propagation: Softwood cuttings.
Root system: Slightly fleshy.
Soil: All moist but well-drained soils.
Sunlight: Full sun to semi-shade.
Time to initiate rooting: 4–6 weeks are needed to produce roots on an initial cutting.
Temperature to initiate rooting: 20° to 25° Centigrade air temperature.
Crop time: 12 months are needed to produce a finished 1-liter container from a rooted cutting.
Seasonal interest: Light purple flowers in spring and early summer.
Disease and pests: Slightly susceptible to mildew.
Stem:
  *Stem diameter.*—0.4 cm. in diameter.
  *Stem length.*—1.8 meters in length, or much less.
  *Surface.*—Ribbed, with short grayish hairs.
  *Lenticels.*—None present.
  *Stem color.*—200D.
  *Internode length.*—6–15 cm. between nodes.
  *Branching habit.*—Basal shoots.
Foliage:
  *Type.*—Deciduous.
  *Leaf arrangement.*—Opposite.
  *Leaf division.*—Simple or ternate.
  *Leaf attachment.*—Petiolate.
  *Leaf dimensions.*—1.0 cm–4.5 cm. in length and 0.8 cm.–2.5 cm. in width.
  *Leaf shape.*—Lanceolate.
  *Leaf base.*—Oblique.
  *Leaf apex.*—Acute.
  *Leaf venation.*—Palmate.
  *Leaf margin.*—Entire and sometimes lobed.
  *Leaf color* (*adaxial surface*).—137A.
  *Leaf color* (*abaxial surface*).—137D.
  *Vein color* (*adaxial surface*).—147D.
  *Vein color* (*abaxial surface*).—147D.
  *Leaf surface* (*adaxial*).—Glabrous.
  *Leaf surface* (*abaxial*).—Sub-glabrous and slightly reticulate.
  *Petiole dimensions.*—Up to 3 cm in length, 0.2 cm in diameter.
  *Petiole color.*—147B.
  *Petiole surface.*—Sparsely hairy.
Flower:
  *Blooming season.*—Summer.
  *Inflorescence type.*—Few-flowered dichasial cyme.
  *Flower arrangement.*—Spiral.
  *Color of peduncle.*—59B.
  *Peduncle length.*—5 cm–20 cm in length.
  *Peduncle width.*—0.15 cm. in width.
  *Peduncle surface.*—Sparse short hairs.
  *Self-cleaning or persistent.*—Self-cleaning.
  *Diameter of flower.*—8 cm at widest aspect.
  *Depth of flower.*—4 cm.
  *Flower shape.*—Campanulate.
  *Aspect.*—Nodding.
  *Petals.*—Apetalous.
  *Tepals.*—Four tepals.
  *Tepal shape.*—Obovate-oblanceolate.
  *Tepal apex.*—Acute.
  *Tepal base.*—Truncate.
  *Tepal surface* (*upper surface*).—Glabrous with villous margin.
  *Tepal surface* (*lower surface*).—Glabrous.
  *Tepal margin.*—Slightly crenulate.

*Tepal length.*—4 cm. in length.
*Tepal width.*—1 cm. in width.
*Color of tepal* (*adaxial surface*).—N74A at base extending to, and becoming slightly paler, N74B, at apex. Coloration presents lanceolate effect in contrast with lower tepal margin and lobes which are colored N74D.
*Color of tepal* (*abaxial surface*).—N74B at base becoming N74C.
*Unfused or fused.*—Tepals are unfused.
*Calyx.*—Absent.
*Bud color.*—Dark red-purple.
*Bud shape.*—Ovate.
*Bud dimensions* (*just before opening*).—3 cm. in length and 0.8 cm. in width.
*Quantity of flowers per branch.*—Approximately 15–25 flowers per branch.
*Lastingness of flower.*—An individual flower with last 10 days on the plant (from bud to tepals falling off) and 5–8 days off the plant.
*Fragrance.*—Slightly sweet.

Reproductive organs:
*Stamens.*—Approximately 50 in number.
*Color of stamens.*—Yellow.
*Dimensions of stamen.*—0.4–0.7 cm. in length and 0.1 cm. in width.
*Dimensions of anther.*—10 mm. in width and 30 mm. in length.
*Pollen color.*—Pale yellow.
*Amount of pollen.*—Large amount.
*Anther color.*—Cream.
*Anther shape.*—Linear.
*Pistils.*—Approximately 25.
*Pistil shape.*—Plumose.
*Pistil color.*—White.
*Stigma shape.*—Simple.
*Stigma color.*—White.
*Style color.*—Green with white hairs.
*Ovary position.*—Superior.
*Ovary color.*—Green.

Seed:
*Number of seeds.*—Approximately 2–3 seeds per flower.
*Seed shape.*—Orbicular.
*Seed color.*—First green, then turning dark brown.
*Seed dimensions.*—0.5 cm. in length and 0.6 cm. in width.

It is claimed:

1. A new and distinct variety of *Clematis* plant named 'Hendryetta' as described and illustrated.

* * * * *